(12) United States Patent
Turner et al.

(10) Patent No.: US 9,958,427 B2
(45) Date of Patent: May 1, 2018

(54) REVERSE FILLING CARBON AND TEMPERATURE DROP-IN SENSOR

(71) Applicant: Heraeus Electro-Nite International N.V., Houthalen (BE)

(72) Inventors: Paul A. Turner, Milwaukee, WI (US); Harry G. Clauss, Jr., Delanco, NJ (US)

(73) Assignee: Heraeus Electro-Nite International N.V., Houthalen (BE)

( * ) Notice: Subject to any disclaimer, the term of this patent is extended or adjusted under 35 U.S.C. 154(b) by 280 days.

(21) Appl. No.: 14/942,180

(22) Filed: Nov. 16, 2015

(65) Prior Publication Data

US 2016/0209341 A1    Jul. 21, 2016

Related U.S. Application Data

(60) Provisional application No. 62/105,882, filed on Jan. 21, 2015.

(51) Int. Cl.
*G01N 33/20* (2006.01)
*G01K 7/02* (2006.01)
*B22D 2/00* (2006.01)
*G01N 1/12* (2006.01)

(52) U.S. Cl.
CPC ........... *G01N 33/206* (2013.01); *B22D 2/006* (2013.01); *G01K 7/02* (2013.01); *G01N 1/125* (2013.01)

(58) Field of Classification Search
CPC ...... G01N 33/206; G01N 1/125; B22D 2/006; G01K 7/02
See application file for complete search history.

(56) References Cited

U.S. PATENT DOCUMENTS

| | | | |
|---|---|---|---|
| 3,357,598 A | 12/1967 | Kraft | |
| 3,374,122 A | 3/1968 | Cole | |
| 3,463,005 A | 8/1969 | Hance | |
| 3,559,452 A | 2/1971 | Perbix et al. | |
| 3,574,598 A | 4/1971 | Kern et al. | |
| 3,813,944 A * | 6/1974 | Ryntz, Jr. | G01K 13/125 374/179 |
| 3,950,992 A * | 4/1976 | Hance | G01N 1/125 374/140 |

(Continued)

FOREIGN PATENT DOCUMENTS

CN    201041556 Y    3/2008

*Primary Examiner* — Lisa Caputo
*Assistant Examiner* — Philip Cotey
(74) *Attorney, Agent, or Firm* — Panitch Schwarze Belisario & Nadel LLP (57) ABSTRACT

A drop-in probe for determining phase changes by thermal analysis of a sample of a molten metal includes a measurement head having a first end which is an immersion end and an opposing second end having an end face. A sample chamber is arranged within the measurement head. An opening, which is free of any restrictions and which is in communication with the sample chamber, is formed in the end face of the second end of the measurement head. The sample chamber includes a first thermocouple having a first thermocouple junction enclosed within a wall which has a uniform internal geometry. A ratio D/H of an internal diameter D of the sample chamber to a length H extending between the opening and the first thermocouple junction is between 0.1 and 1.2.

10 Claims, 7 Drawing Sheets

(56) References Cited

U.S. PATENT DOCUMENTS

| | | | |
|---|---|---|---|
| 4,141,249 A | 2/1979 | Ishikawa et al. | |
| 4,557,152 A * | 12/1985 | Plessers | G01N 1/125 73/864.55 |
| 4,881,824 A | 11/1989 | Falk et al. | |
| 5,033,320 A | 7/1991 | Baerts | |
| 5,198,749 A * | 3/1993 | Guthrie | G01N 15/12 164/4.1 |
| 5,577,841 A | 11/1996 | Wall | |
| 6,454,459 B1 * | 9/2002 | Sillen | G01N 25/18 164/151.4 |
| 9,116,054 B2 | 8/2015 | Beyens | |
| 2011/0308319 A1 * | 12/2011 | Neyens | G01N 1/125 73/700 |
| 2013/0098173 A1 | 4/2013 | Neyens et al. | |
| 2014/0318276 A1 * | 10/2014 | Cappa | G01N 1/125 73/863.11 |

\* cited by examiner

REVERSE FILLING CARBON AND TEMPERATURE DROP-IN SENSOR

CROSS-REFERENCE TO RELATED APPLICATIONS

This application claims the benefit of U.S. Provisional Patent Application No. 62/105,882, filed Jan. 21, 2015, the entire contents of which are incorporated by reference herein.

BACKGROUND OF THE INVENTION

The present invention relates to a drop-in sensor comprising a bath thermocouple and a reverse-filling uniform geometry solidification chamber. The solidification chamber has no restrictions at the fill opening and a minimum dimension from the solidification chamber fill opening to the solidification chamber thermocouple measurement junction. The drop-in sensor according to the present invention allows for rapid and accurate measurements of the liquidus temperatures of molten metals.

During the steelmaking process, oxygen is combined with carbon dissolved in the steel to remove the carbon, while at the same time providing heat from the combustion process. When the carbon content, as well as the molten metal temperature, are known, the furnace operator can decide the extent of additional refining or end the process. It is therefore advantageous to have available information regarding both the temperature of the liquid metal and the carbon content.

U.S. Pat. No. 3,559,452 describes the usefulness and terminology of carbon determination in molten steel during the converter process. It is a common practice to employ disposable immersion sensors, such as those disclosed in U.S. Pat. No. 5,577,841, which are attached to a metal support lance and manually manipulated by an operator to obtain temperature and thermal analysis information. In many instances, ready access to the interior of steel processing vessels in order to contact the molten metal with disposable immersion measuring sensors, and thus determine the temperature and carbon content of the metal, is severely limited.

Large mechanical auxiliary lances, such as those described in U.S. Pat. No. 4,141,249, which are suitable for use in a converter process, have been constructed to immerse multifunctional sensor probes, such as those described in U.S. Patent Application Publication No. 2013/0098173, specially designed to attach to these auxiliary lances. However, there is a large capital expense required to modify an existing converter with an auxiliary lance. Once installed, the on-going maintenance of this equipment is difficult in the industrial environment of a typical steel mill, thereby increasing the cost per measurement. All of these expenses present a barrier to low cost steel production.

Drop-in or thrown-in devices have been developed to avoid the large capital investment of the auxiliary lance. Such measuring devices are dropped into the vessel from an access port well above the molten metal surface. These devices trail a signal cable that relays the thermocouple output to remote instrumentation providing data about the degree of processing accomplished, thereby enabling an operator to judge the extent of further processing required. Such devices for temperature measurement or thermal analysis are described in U.S. Pat. No. 3,357,598 and U.S. Pat. No. 3,463,005.

One difficulty in obtaining consistent and reliable molten metal sensor information from conventional drop-in devices is ensuring that the dropped sensor enters the liquid steel and remains submerged for a duration sufficient to obtain the desired measurements. Specifically, during the refining process, a large amount of slag floats on top of the molten steel and impedes the penetration of the dropped device through the slag layer and into the molten metal. Generally, an object dropped from a height above a liquid body will continue to be submerged below the liquid surface until its terminal velocity approaches zero, its buoyancy force counters the immersion force and the body reverses the trajectory towards floatation. More particularly, if the displaced volume of the molten steel is significantly greater than the weight of the portion of the drop-in sensor designed to be immersed therein, the sensor will float rather than become immersed. The buoyant force acting on the body immersed in the molten steel will act in an upward direction, thereby resulting in a floating position partially or totally above the liquid steel.

It has been traditionally recognized that the random drop of these sensors could, in some circumstances, result in errors when the thermocouple or an opening to a thermal arrest chamber is not orientated for optimal contact with the molten steel. Both a side-extending thermocouple, such as disclosed in U.S. Pat. No. 3,574,598, or a side-opening thermal arrest chamber, such as disclosed in U.S. Pat. No. 3,463,005, could face away from the metal and thus experience errors due to limited molten metal contact, partial filling or not being filled at all as a result of floatation.

To overcome this problem, improvements in these devices typically relied upon the bulk density of the device in relation to that of the liquid slag and that of the liquid steel, so as to aid in the descent of the device through the slag and into the steel, while providing some orientation toward the desired immersion direction. Bulk density is used herein to mean the overall density, including the sensor components and any voids within the overall immersed device and signal cable according to it submersed length. The multiple cross-sections in each configuration shown in U.S. Pat. No. 9,116,054 are graduated to accomplish a preferred orientation. That is, the total bulk density can be less than 7 g/cm$^3$ as long as a dense section of the measuring head has an apparent density greater than 7 g/cm$^3$ necessary to ensure immersion of the measuring elements. Since liquid steel is approximately 90 percent as dense as solid steel, massive void free sections forward of the sensing elements are required to provide this orientation. The measuring elements are thus positioned at a distance removed from the forward face of the sensor. However, a sensing element at the forward face is the exact location that is favored for the longest exposure to the steel to be measured.

Still, at times, when the orientation is correct, that is, placing the temperature sensor in the metal and with a thermal arrest chamber that has filled with liquid metal, there exists a potential that accurate and reliable measurements are not obtained. U.S. Pat. No. 5,033,320 describes the necessary relation of the mass of the cooling chamber to the rate of solidification to obtain accurate thermal arrest information. While the bath temperature can be detected in a relatively short time, a longer time is required for the solidifying metal to reach a stable thermal balance between the released latent heat of fusion and the heat extraction of the cooling mass, and thus to obtain a liquidus plateau. From the detection of the temperature of a stable liquidus plateau, an accurate estimation of the carbon content can be made.

From the time the drop-in sensor is released, the trailing signal cable is constantly combusting. There is a potential for the destruction of the trailing signal cable to advance to a failed state before obtaining a longer duration liquidus plateau, such as that experienced for a high bath temperature, and thus failing to obtain the desired measurement. This is not new to the art. Various isolative and protective strategies have been employed in prior devices to delay the destruction of the signal cable by surrounding a portion of the signal cable exiting the measuring head with tubes of refractory material or cardboard, such as in U.S. Pat. No. 3,374,122

It is suggested by U.S. Pat. No. 4,881,824 that when the measurement head has an adjustable low density tube float on its end facing away from the immersion end and the signal cable is guided through this tube, such an arrangement provides for sufficient protection of the signal cable to obtain the desired measurements. At the same time, the low density material also serves as a counterbalance, orientating the measuring head and stabilizing it in a down-facing position. Although the float should orient the measuring device in a sensor element downward position, this is only true in a mono-density fluid. In the typical steel making vessel, where the slag typically has a density of approximately 3 g/cm$^3$ and the steel typically has density of nearly 7 g/cm$^3$, float-equipped devices have an overall bulk density that is much less than that of the liquid steel yet greater than that of the slag. Any additional buoyant material may orient the sensor within the first, less dense liquid layer, but no quantity of float will force a lower density measuring head to submerse itself below the second, higher density liquid.

Figure 2:
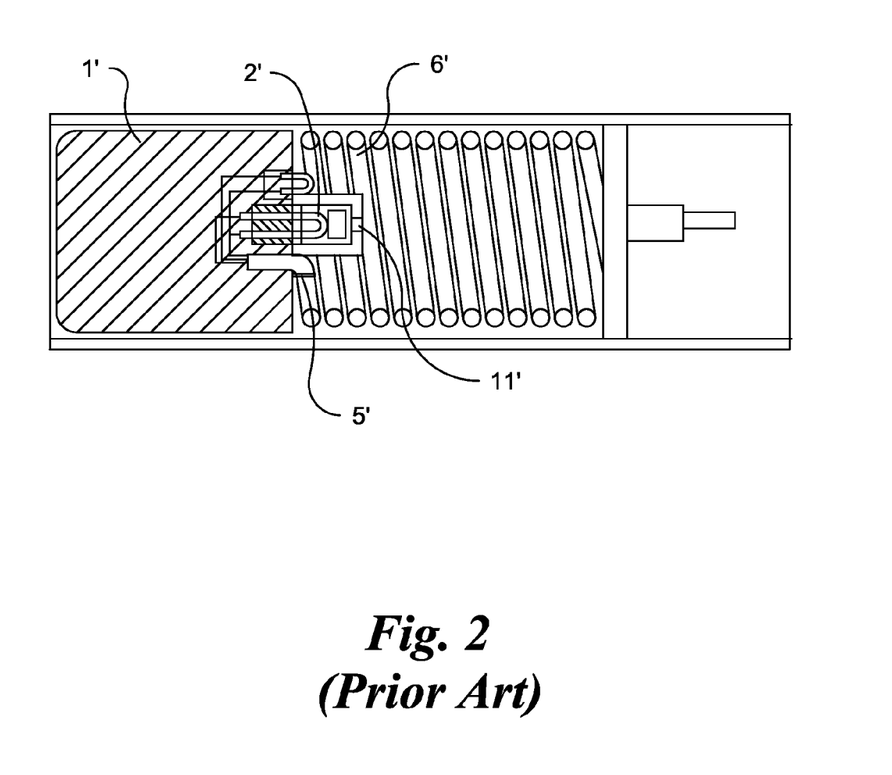
FIG. 2 is a cross-sectional view of a measurement head according to the prior art.

Some known prior art drop-in devices include a rear-filling solidification chamber (i.e., the opening to the thermal arrest sample chamber is opposite to the immersion end), such as the device of Chinese Patent No. 201041556 (shown in FIG. 2). The chamber 2' is constructed of resin sand and is axially located. However, because the chamber 2' contains molten metal in contact with its inner wall and it outer wall is directly exposed to the molten bath, the chamber 2' has an inefficient thermal capacity to chill the metal that has entered the inlet 11'. Without complete thermal isolation of the sample chamber 2', the molten metal bath may act as a heat pump, thereby heating the liquid phase of the solidifying mass in the chamber 2' and resulting in liquidus measurement errors which increase in number and magnitude as the molten metal superheat increases. In the conventional sense, superheat is determined by the difference between the temperature of the molten metal at the time of sampling and the thermal arrest temperature detected during its solidification. Accordingly, when a large portion of the sample chamber 2' exists outside of the main measurement head 1' and is in thermal communication with the molten metal bath, as shown in the prior art device of FIG. 2, it is subject to direct heating from the molten metal bath, thus diminishing the cooling ability of the sample chamber 2' materials. Also, the exit of the signal cable 6 is secured to the measurement head 1 by a metal ring 5', but is not restricted in its lateral movements, such that the sample chamber 2' may be destroyed in certain orientations.

In some prior art drop-in probes, the solidification or sample chamber inflow/inlet opening is typically restricted and surrounded by a chilling mass which chills the inlet opening before the onset of solidification of the chamber contents, thus separating the potential of heat flux from the hotter surrounding liquid metal from delaying chilling or, at worst, reheating the remaining liquid of the two-phase solidifying mass.

Incremental improvements to drop-in measuring probes have eliminated many expected failure modes. However, many of these techniques are suitable only for drop-in devices when the time of the desired measurement occurs at the end of the converter process. This is disadvantageous, because a measurement of the temperature and carbon content is most desired prior to the end of the process, namely during the blowing process. It is at this time that adjustments to the process could be effected based on knowledge of the in-blow temperature and carbon content. There are numerous conditions at an intermediate measurement time, that is during blowing, which escalate the difficultly of a drop-in sensor penetrating and passing into the metal at a suitable depth in order to acquire reliable measurements. With the exception of the few previously mentioned devices, most of the known prior art is absent of improvements which address the difficultly of using drop-in sensors to obtain "in-blow" measurements.

Toward the end of decarburization, the amount of iron oxide transferred to the slag increases and thus reduces the viscosity, allowing for less drag, a reduction in slag volume due to the release of emulsified gases, and a leveling of the liquids at the end of blowing. All of these benefits are not available to those sensors dropped at in-blow. A large volume of slag that the sensor must pass through and a more viscous slag tend to delay the exposure of the thermocouple to the steel and delay the opening of the solidification chamber. Previously employed floats can impede that passage of the measuring head through the slag. Delays in passing through the slag promote freezing of the slag to the sensor's metal components, and thus increase the apparent volume and reduces bulk density. Retention of the desired submerged position is highly compromised.

An objective of the present invention is to provide a cost efficient drop-in sensor for use in a steelmaking vessel during and prior to the end of the blowing process for providing "in-blow" measurements. More particularly, in order to correct the deficiencies of prior art devices and extend the usefulness of drop-in sensors to "in-blow" measurements, the present invention employs a design based upon the kinetic potential of a weighted falling body to penetrate the liquid layers with an adequate submersion momentum, so as to remain below the slag metal interface for a critical duration. A measurement head according to an embodiment of the present invention has an in-situ density which is achieved by rapid filling of the solidification chamber during the initial descent into the liquid metal. Preferably, the rapid filling eliminates the initial void, and thus retards the normal buoyance-driven time to surface to measuring head. Once the liquidus chamber has been filled, the liquidus arrest plateau may occur even while the measurement head has surfaced, while providing a necessary time interval to obtain the required temperature measurement before floatation.

BRIEF SUMMARY OF THE INVENTION

In one embodiment, the present invention is directed to a drop-in probe for determining phase changes by thermal analysis of a sample of a molten metal. The drop-in probe includes a measurement head having a first end which is an immersion end and an opposing second end having an end face, and a sample chamber arranged therein. An opening, which is free of any restrictions and which is in communication with the sample chamber, is formed in the end face of the second end of the measurement head. The sample chamber includes a first thermocouple having a first thermocouple junction enclosed within a wall which has a uniform internal geometry. A ratio D/H of an internal diameter D of the sample chamber to a length H extending between the opening and the first thermocouple junction is between 0.1 and 1.2.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIGS. 6-1 and 6-2 illustrate how the bulk and in-situ densities, respectively, of the measurement head are calculated according to an embodiment of the present invention.

DETAILED DESCRIPTION OF THE INVENTION

The present invention relates to a drop-in probe 10 for determining phase changes by thermal analysis of a sample obtained from a molten steel bath. In use, the drop-in probe 10 is positioned at a predetermined height above a metallurgical melting vessel and released so as to fall into the metallurgical melting vessel from the predetermined height. The drop-in probe 10, and more particularly a measurement head 12 of the drop-in probe 10, plunges into the molten metal (e.g., molten steel) after passing through and penetrating a slag layer lying above the molten metal. The drop-in probe 10 is connected to a signal cable 3 by which measurement signals can be led to suitable instrumentation, not shown. In use, the signal cable 3 remains attached to the instrumentation.

Figure 1:
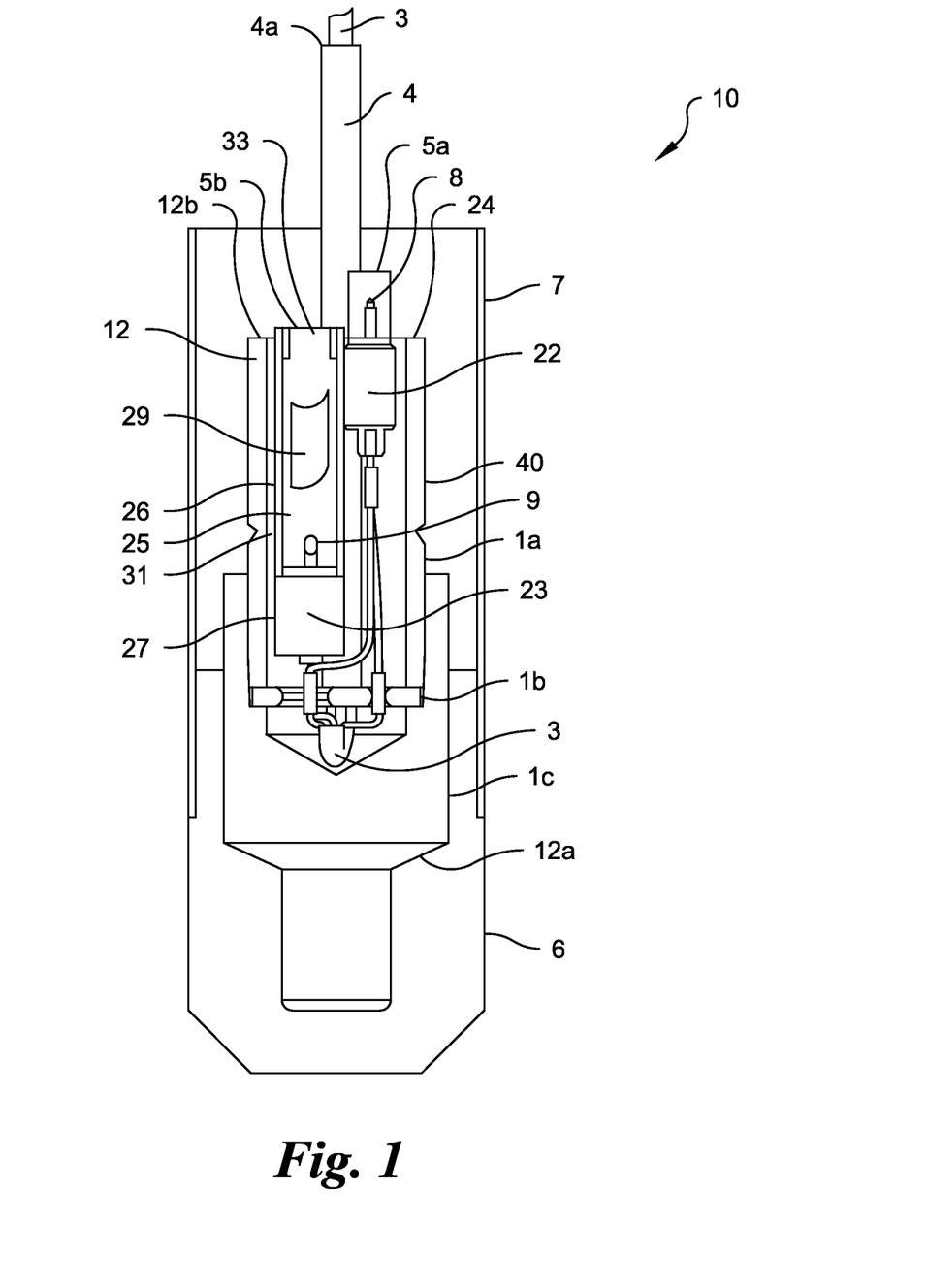
FIG. 1 is a front elevational view of the measurement head according to an embodiment of the present invention.
Figure 3:
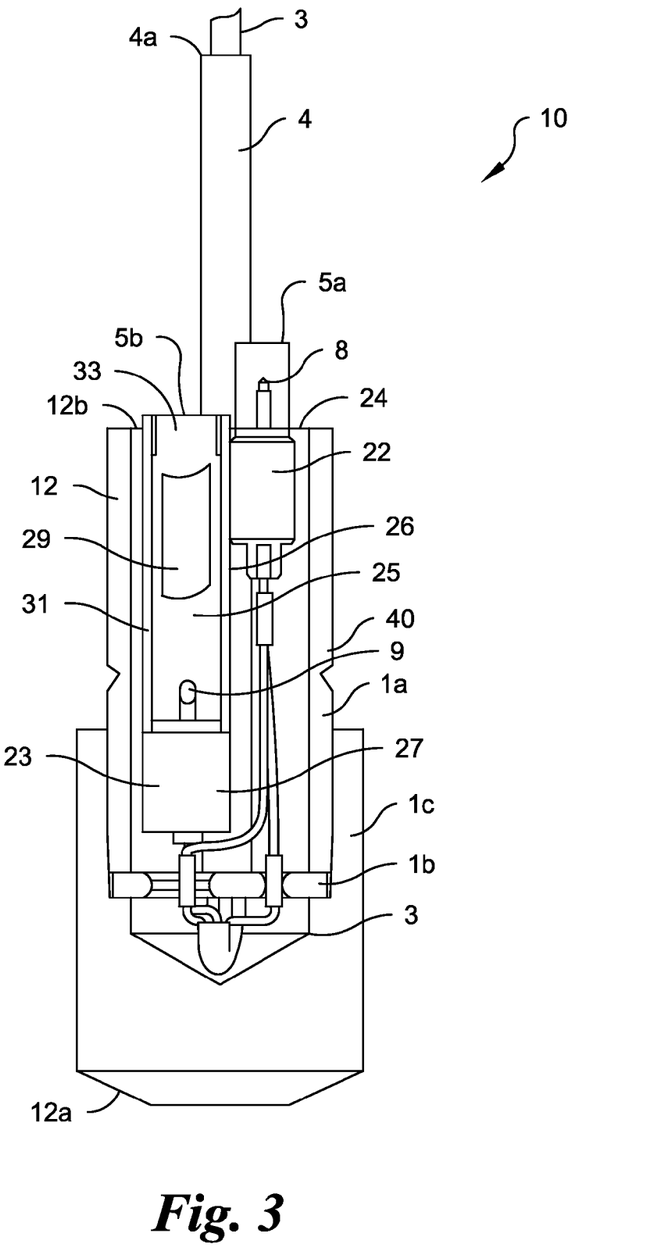
FIG. 3 is a front elevational view of the measurement head according to an embodiment of the present invention, with select components omitted.

In one embodiment, as shown in FIGS. 1 and 3, the present invention relates to a measurement device, and more particularly a drop-in probe 10, having a measurement head 12 comprising a compound metal housing 40 made of a first component 1$a$, a second component 1$b$ and a third component 1$c$. The first and third components 1$a$ and 1$c$ are forcibly fit together capturing component 1$b$. The measurement head 12 preferably includes a first end 12$a$ which is an immersion end and an opposing second end 12$b$ having an end face or surface 24. A cushion cap 6, preferably made of a polymer (and more preferably Styrofoam®), is preferably attached to the immersion face or end 12$a$.

The measurement head 12 further includes an extension tube 4 which passes through the first component 1$a$ and emerges from the end face 24, opposite the immersion end 12$a$, of the measurement head 12. The signal cable 3 is guided through the extension tube 4 and exits therefrom at an outlet opening 4$a$. The extension tube b 4 protects the signal cable 3 from early damage due to the slag or the molten steel. The extension tube 4 may be made of a metal, such as steel, or of a plastic, a rubber, a paper material or a woven material. Preferably, the extension tube 4 is made of a metal. The extension tube 4 may be stiff or flexible.

Assembled within the measurement head 12 is a solidification or sample chamber assembly 31, as shown in FIGS. 1 and 3, including a solidification or sample chamber 25. The sample chamber 25 is a thermal arrest sample chamber (i.e., the sample chamber 25 is thermally isolated from the mass of the measurement head 12) and is preferably arranged opposite the immersion end 12$a$ of the measurement head 12. The solidification chamber assembly 31 includes a chamber wall 26, which is preferably tubular and which chills the sample chamber 25. As such, the chamber wall 26 is a chilling mass. The sample chamber 25 preferably has a uniform geometry with no changes in dimension along a length L of the sample chamber 25.

The solidification chamber assembly 31 also includes a first thermocouple assembly 23 positioned to measure the liquidus temperature of the solidifying metal contained in the sample chamber 25 and a first thermocouple assembly housing 27 which supports the first thermocouple assembly 23. More particularly, a first thermocouple junction 9 of the first thermocouple element 23 projects from the first thermocouple assembly housing 27 and into an interior of the sample chamber 25 for measurement of the sample's solidification temperature. The first thermocouple assembly housing 27 is preferably made from a heat activated foundry resin sand.

Preferably, a deoxidant material 29 is arranged in the sample chamber 25. In one embodiment, the deoxidant material 29 is aluminum, and more preferably 0.5 g of aluminum foil.

The measurement head 12, and more particularly the sample chamber assembly 31, further includes an opening 33 configured to receive the molten metal for filling the sample chamber 25. That is, once submersed in the molten metal bath, the molten metal enters the sample chamber 25 through the opening 33. The opening 33 is preferably arranged at the second end 12$b$ of the measurement head 12 opposite the immersion end 12$a$, and more particularly is formed as an opening in the end face 24. Accordingly, the sample chamber 25 is a rear-filling or reverse-filling thermal arrest sample chamber. The sample chamber 25 preferably has a uniform diameter D, and more particularly the wall 26 preferably has a uniform internal diameter D, extending from the opening 33 to a bottom wall of the chamber 25.

Figure 5:
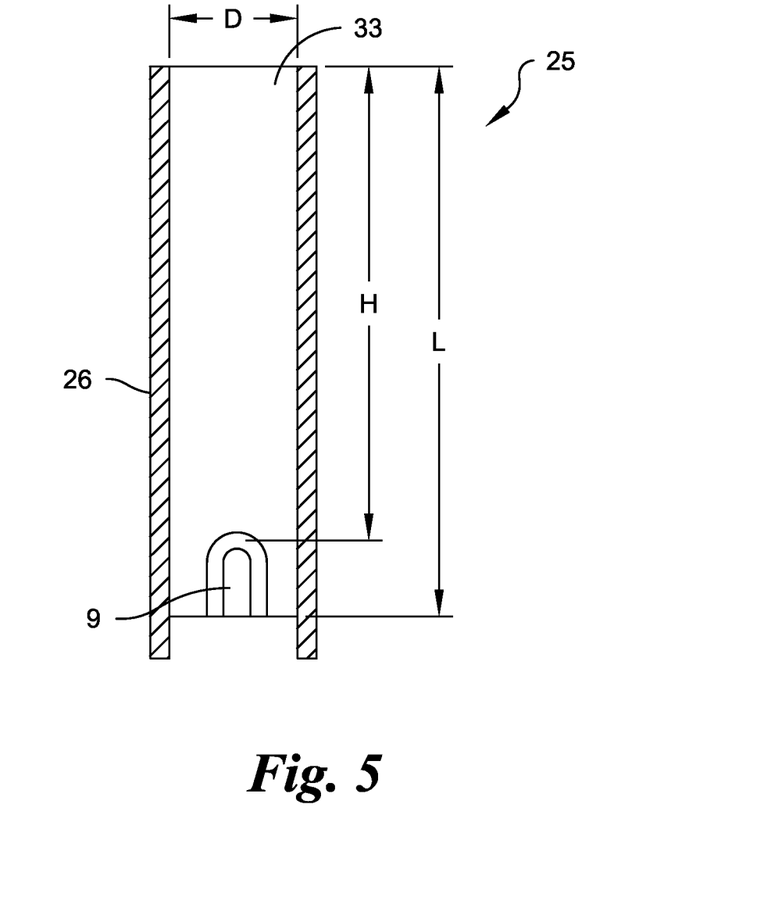
FIG. 5 is a front elevational view of the solidification chamber of the measurement head according to an embodiment of the present invention.

The opening 33 is preferably a large and unrestricted opening. More particularly, has been surprisingly found that the filling delay caused by restrictions in prior art devices may be eliminated, while and at the same time, achieving the benefit of avoiding thermal exchange with the molten metal bath and high liquidus measurement accuracy, by maintaining the distance H between the sample chamber opening 33 and the sample chamber thermocouple measuring junction 9 as a predetermined ratio with respect to the diameter D of the sample chamber 25, and more particularly the diameter D of the sample chamber opening 33. More particularly, a ratio D/H of the length or height H of the sample chamber 25 above the sample chamber thermocouple junction 9 with respect to the diameter D of the sample chamber 25 is preferably between 0.1 and 1.2, and more preferably 0.3, as shown in FIG. 5. Using the ratio D/H and selecting the metal mass of the sample chamber wall 26 so that heat extracted in the area of the sample chamber thermocouple assembly 23 is greater than the reheating of the surrounding liquid metal, it has been surprisingly found preferable to maintain a ratio of the chilling mass 26 to the mass of the molten metal contained in the sample chamber 25 to be between 0.25 and 1.25, which is much less than what is taught by the known prior art (e.g., U.S. Pat. No. 5,033,320). In one embodiment, the diameter D of the sample chamber 25 is preferably approximately 19 mm.

Combining the factor of the predetermined ratio D/H with an adequate chilling mass of the sample chamber wall 26, the drop-in probe 10 of the present invention allows for accurate bath carbon and corresponding liquidus measurements in bath carbons levels of 0.1% to 1.0% and bath superheats levels of 40° C. to 170° C., using a rear-filling solidification chamber 25.

On one end of the measurement head 12, and more particularly proximate the second end 12b opposite from the immersion end 12a, is an additional or second thermocouple assembly 22 having a second thermocouple junction 8 positioned to measure the molten metal bath temperature. More particularly, the second thermocouple junction 8 projects out of the housing 40 of the measurement head 12 and away from the end face 24 opposite the immersion end 12a, and preferably extends at least 12.7 mm from the end face 24 in a direction opposite to or reverse from the immersion end 12a of the measurement head 12. The first component 1a partially surrounds both the first and second thermocouple assemblies 23, 22.

The signal cable 3, containing electrical conductors or lead wires, extends from the measurement head 12 to instrumentation to relay the output of first thermocouple element 23 and the output of the second thermocouple element 22 to the instrumentation. The instrumentation, in turn, may display the bath temperature and solidification temperature, and hence the carbon content of the molten metal. The signal cable 3 conductors may be single paired conductors or may have a common conductor. The signal cable 3, the outputs, the receiving connectors and the instrumentation are known in the art.

The drop-in probe 10 further comprises a first protective cap 5a, a second protective cap 5b, and a protective paperboard tube 7, all of which (along with the cushion cap 6) are external to the compound metal housing 40 of the measurement head 12. The first protective cap 5a covers the protruding second thermocouple junction 9 of the second bath thermocouple assembly 22. The first protective cap 5a is preferably made of metal, and more preferably of steel. The second protective cap 5b covers the sample chamber fill opening 33. The second protective cap 5b is preferably made of metal, and more preferably aluminum.

Figure 4:
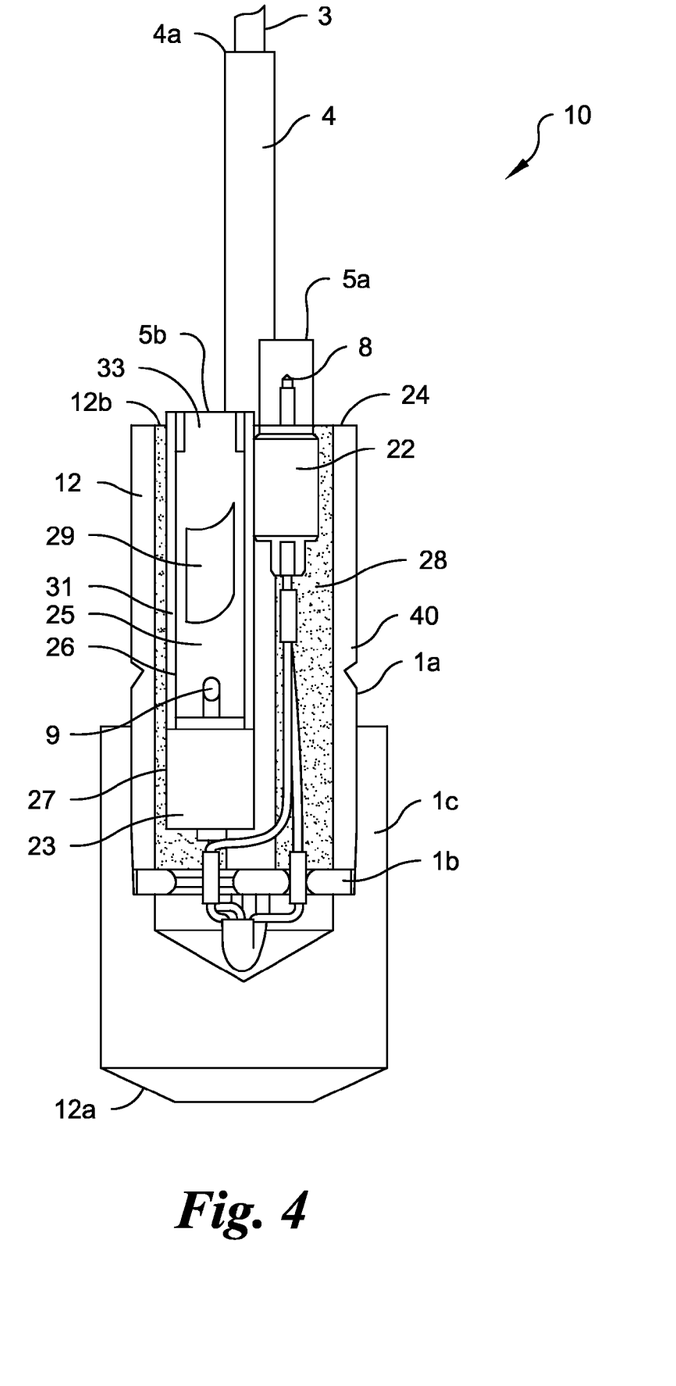
FIG. 4 is a front elevational view of the measurement head shown in FIG. 3, including a back-fill material.

The unoccupied volume of the compound housing 40 of the measurement head 12 is preferably filled with a back-fill fixation material 28, as shown in FIG. 4. The back-fill fixation material 28 is preferably made from heat activated foundry resin sand.

When the measurement head 12 is dropped into molten metal, the momentum of the falling weight of the measurement head 12 results in the immersion of the measurement head 12, and more particularly of the end face 24, beneath the surface (and slag) of the molten metal bath. As such, the drop-in probe 10 of the present invention utilizes the natural force achieved by the measurement head 12 being dropped from a certain height above a molten metal bath. Upon immersion, the first and second protective caps 5a and 5b and the cushion cap 6 are melted or otherwise consumed, thereby exposing the second bath thermocouple element 8 to the molten metal for measurement of the temperature thereof and for allowing molten metal to enter and fill the sample chamber 25 via the opening 33.

During the time from initial immersion until floatation, the measurement head 12 of the present invention achieves a depth necessary for a complete inflow of molten metal into the sample chamber 25 and for obtaining a liquidus measurement and an accurate measurement of the bath temperature. More particularly, the absence of any sort of restriction in the opening 33 of the sample chamber 25 results in unrestricted flow of the molten metal into the sample chamber 25, and thus rapid filling of the chamber 25 with molten metal and the onset of solidification is achieved before the floatation of the measurement head 12 due to buoyant forces.

Accordingly, in one aspect, the present invention relates to a drop-in probe 10 comprising a thermal arrest sample chamber 25 with a large, unrestricted opening 33 and no size changes along the length L of the sample chamber 25. The uniform geometry of the thermal arrest sample chamber 25 minimizes any restriction to molten metal inflow, minimizes the occurrence of trapped pockets of air, and allows the sample chamber 25 to fill with molten metal in situations where low amounts of ferrostatic pressure are present. This characteristic is advantageous, especially in drop-in probe applications where there is no direct control over probe orientation or immersion depth. As such, the large chamber opening 33 and uniform geometry of the thermal arrest sample chamber 25 allow the thermal arrest sample chamber 25 to fill with molten steel rapidly and allow the steel sample to solidify rapidly in order to rapidly obtain a liquidus and bath carbon measurement, preferably within six seconds or less. The beginning of the measurement is preferably taken from the time the measurement head 12 enters the molten metal.

As the sample chamber 25 fills, the initially empty volume of the chamber 25 is replaced by buoyant neutral metal (e.g., steel) and, from this time onward, the in-situ density of the measurement head 12 governs the rate of rise thereof. Quickly achieving the requisite in-situ density is paramount for obtaining a liquidus measurement before the signal cable 3 destructs. Accordingly, as discussed above, in order to ensure a rapid and uniform flow of the liquid molten metal into the sample chamber 25, any restrictions at the chamber opening 33 are preferably removed. In one embodiment, one or more gas removal openings may be provided along the entire exhaust pathway.

The total bulk density of the measurement head 12 (i.e., all components making up the measurement head 12, including the extension tube 4 but not the signal cable 3) is preferably less than 7 g/cm$^3$, and more preferably the working density in all cross-sections is less than 7 g/cm$^3$. The sample chamber 25 is preferably unbounded by an inlet restriction and a chill mass separating it from the influence of the molten bath, such that the in-situ density of the measurement head 12, with the sample chamber 25 empty, is preferably greater than 5 g/cm$^3$. Upon filling of the sample chamber 25, the in-situ density of the measurement head 12 is preferably less than 6.5 g/cm$^3$, as shown in Example 1 of Table 1. Rapid filling of the sample chamber 25 decreases the open internal volume rapidly, and thus the added density provides for a rapid reduction of the buoyant force and lengthening of the time until floatation of the measurement head 12.

Figure 61:
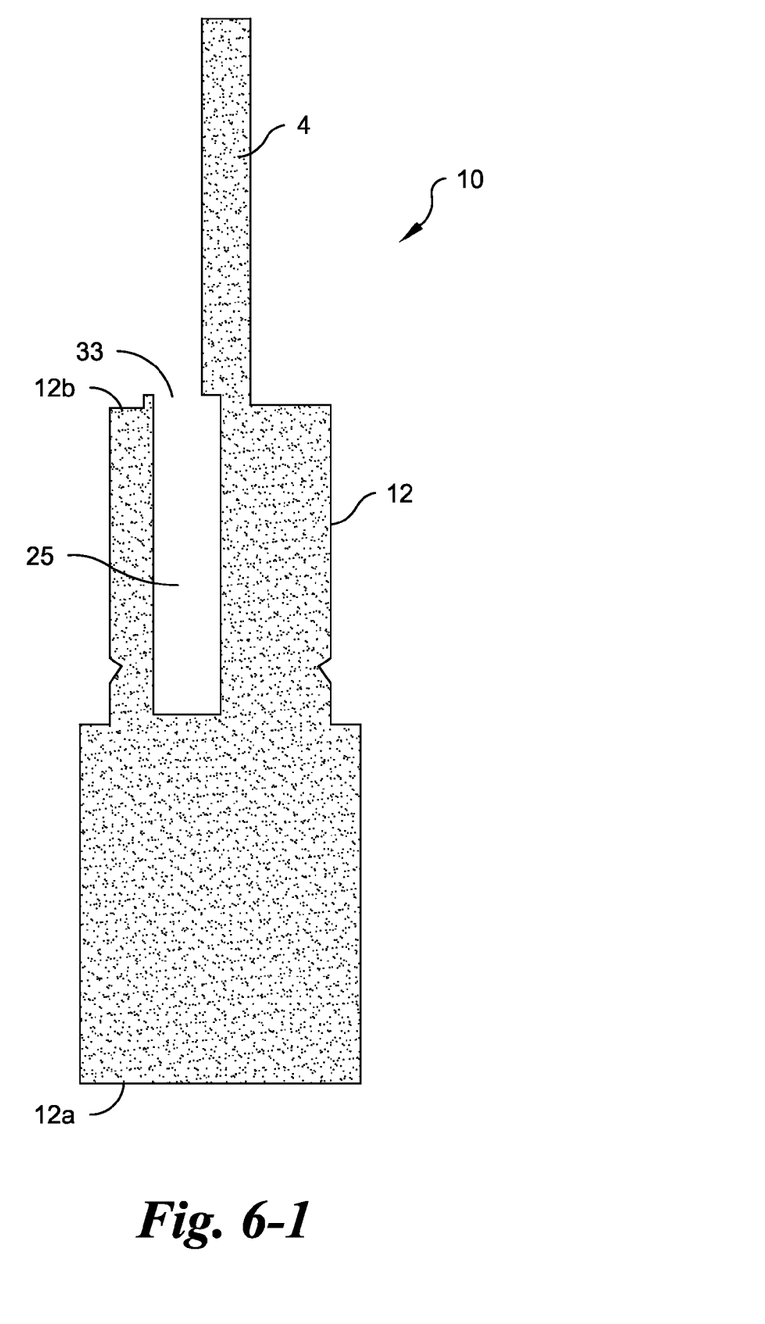
Figure 62:
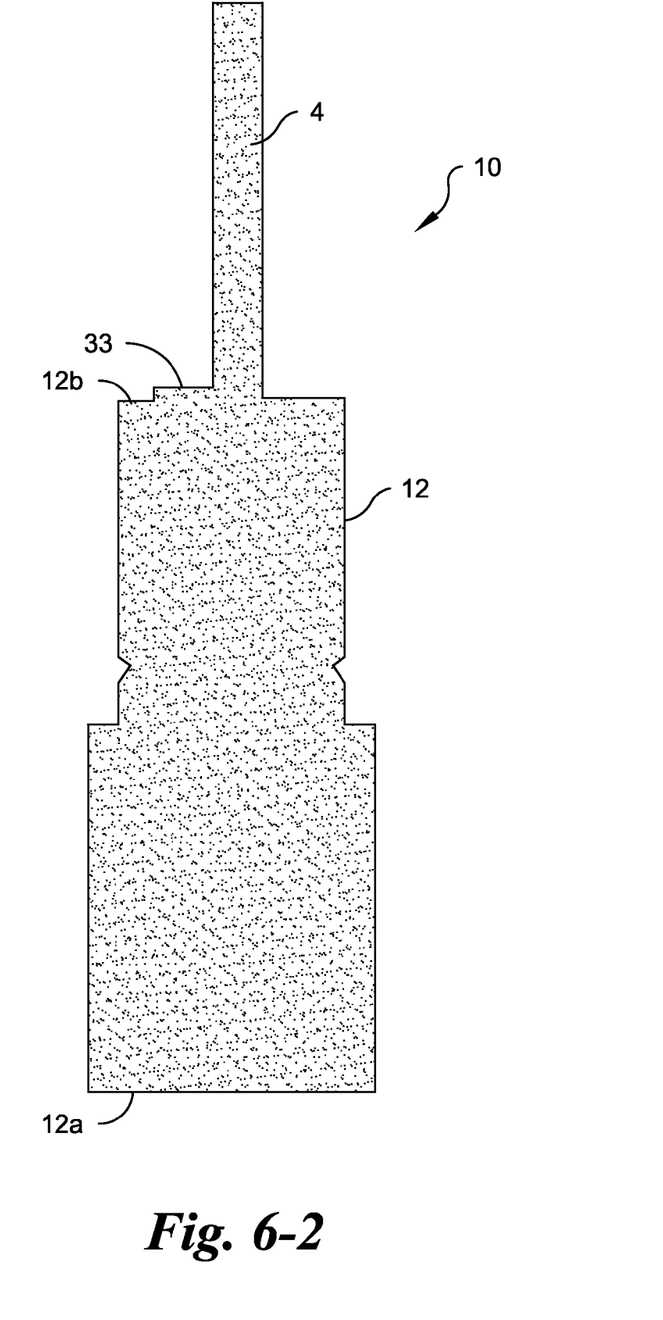

More particularly, FIGS. 6-1 and 6-2 and Table 1 demonstrate the method used to calculate the bulk density and the in-situ density for one configuration of the measurement head 12 in accordance with an embodiment of the present invention.

FIG. 6-1 depicts the volume of the measurement head 12 of Examples 1 and 2 which is used for the initial calculation of bulk density. The gray portion represents the volume of molten metal which is displaced by the measurement head 12 before the sample chamber 25 is filled with molten metal. In Example 1, the displaced volume is approximately 688 cm$^3$. Since the unfilled sample chamber 25 does not have any associated weight (i.e., because it is unfilled), the starting bulk density of the measurement head 12 (i.e., upon being dropped) is 5.8 g/cm$^3$. FIG. 6-2 depicts the volume of the measurement head 12 which is used for a calculation of working in-situ density. The gray portion represents the volume of molten metal which is displaced by the measurement head 12 with a sample chamber 25 that is filled with molten metal. In Example 1, the filled measurement head 12 weighs approximately 4201 g and based on the displaced volume, the in-situ density is now 6.1 g/cm$^3$.

TABLE 1

| Example 1 | |
|---|---|
| Weight of assembled measurement head, empty sample chamber | 3953 g |
| Volume of assembled measurement head, empty sample chamber | 688 cm$^3$ |
| Bulk Density | 5.8 g/cm$^3$ |
| Weight of assembled measurement head, filled sample chamber | 4201 g |
| In-situ density | 6.1 g/cm$^3$ |
| Example 2 | |
| Weight of assembled measurement head, empty sample chamber | 4316 g |
| Volume of assembled measurement head, empty sample chamber | 733 cm$^3$ |
| Bulk Density | 5.9 g/cm$^3$ |
| Weight of assembled measurement head, filled sample chamber | 4564 g |
| In-situ density | 6.2 g/cm$^3$ |

The drop-in probe 10 of the present invention allows for accurate bath temperatures and bath carbon measurements to be made under the in-blow conditions in a steelmaking converter. The drop-in probe 10 of the present invention has been trialed and found to produce measurements during the blow in both top blown (LD, BOP, BOF) converters and bottom blown (Q-BOP, OBM) converters. The unrestricted, uniform geometry thermal arrest chamber 25 design of the present invention allows the probe 10 to be filled in an environment where probe orientation and immersion depth are uncontrolled. An added benefit of the thermal arrest chamber 25 design is the rapid filling and solidification of the metal sample in the chamber 25 resulting in a liquidus and bath carbon measurement in preferably less than six seconds, well below the lifetime of the signal cable 3.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A drop-in probe for determining phase changes by thermal analysis of a sample of a molten metal, the drop-in probe comprising:
    a measurement head including a first end which is an immersion end and an opposing second end having an end face; and
    a sample chamber arranged within the measurement head, an opening in communication with the sample chamber being formed in the end face of the second end of the measurement head, the opening being free of any restrictions, the sample chamber including a first thermocouple having a first thermocouple junction enclosed within a wall, the wall having a uniform internal geometry,
    wherein, a ratio D/H of an internal diameter D of the sample chamber to a length H extending between the opening and the first thermocouple junction is between 0.1 and 1.2, and
    wherein, when the sample chamber is filled with a sample of the molten metal, a ratio of a mass of the metal accommodated in the sample chamber to a mass of the wall of the sample chamber is between 0.25 and 1.25.

2. The drop-in probe according to claim 1, wherein the ratio D/H is 0.3.

3. The drop-in probe according to claim 1, further comprising a second thermocouple having a second thermocouple junction at the immersion end of the measurement head.

4. The drop-in probe according to claim 1, further comprising an extension tube emerging from second end of the measurement head and a signal cable extending through the extension tube and exiting therefrom at an outlet opening.

5. The drop-in probe according to claim 4, wherein the extension tube is made of a material selected from the group consisting of a metal, a plastic, a rubber, a paper material and a woven material.

6. The drop-in probe according to claim 1, wherein an in-situ density of the measurement head, with the sample chamber being empty, is greater than 5 g/cm$^3$.

7. The drop-in probe according to claim 1, wherein an in-situ density of the measurement head, with the sample chamber being filled with the molten metal, is less than 6.5 g/cm$^3$.

8. The drop-in probe according to claim 1, further comprising a cushion cap attached to the immersion end.

9. The drop-in probe according to claim 1, further comprising a protective cap covering the opening.

10. The drop-in probe according to claim 9, wherein the cap is made of aluminum.

\* \* \* \* \*